United States Patent
Sorensen et al.

(10) Patent No.: US 7,968,351 B2
(45) Date of Patent: Jun. 28, 2011

(54) METHOD FOR DISSOLUTION TESTING OF PHARMACEUTICAL PRODUCTS

(75) Inventors: Lise Smith Sorensen, Helsinge (DK); Anne Piechowicz Schwartz, Hellerup (DK); Jan Sondergaard-Andersen, Hillerod (DK)

(73) Assignee: ALK-Abello A/S, Horsholm (DK)

( * ) Notice: Subject to any disclaimer, the term of this patent is extended or adjusted under 35 U.S.C. 154(b) by 254 days.

(21) Appl. No.: 12/158,913

(22) PCT Filed: Dec. 22, 2006

(86) PCT No.: PCT/DK2006/000739
§ 371 (c)(1), (2), (4) Date: Jun. 23, 2008

(87) PCT Pub. No.: WO2007/071257
PCT Pub. Date: Jun. 28, 2007

(65) Prior Publication Data
US 2008/0305505 A1    Dec. 11, 2008

Related U.S. Application Data

(60) Provisional application No. 60/753,714, filed on Dec. 23, 2005.

(30) Foreign Application Priority Data

Dec. 23, 2005  (DK) .................................. 2005 01828

(51) Int. Cl.
*G01N 33/00*    (2006.01)
(52) U.S. Cl. ............................................ 436/536; 436/8
(58) Field of Classification Search ........................ None
See application file for complete search history.

(56) References Cited

U.S. PATENT DOCUMENTS 5,382,601 A * 1/1995 Nurnberg et al. ............. 514/775
6,132,759 A   10/2000 Schacht et al.

FOREIGN PATENT DOCUMENTS

| WO | WO-2004047794 | 6/2004 |
| WO | WO-2004051263 | 6/2004 |
| WO | WO-2004079338 | 9/2004 |
| WO | WO-2005/114214 | 12/2005 |

OTHER PUBLICATIONS

Bayomi et al. Pharmaceutica Acta Helvetiae 1998 vol. 73, p. 187-192.*
Heya et al. (J. Pharmaceutical Sciences 1994 vol. 83, p. 636-640).*
Blanco-Prieto M J et al., "Importance of the test medium for the release kinetics of a somatostatin analogue from poly(D,L-lactide-co-glycolide) microspheres." International Journal of Pharmaceutics (1999), vol. 184, No. 2, pp. 243-250.
European Pharmacopeia 5.0, 2.9.3. Dissolution Test for Solid Dosage Forms, pp. 228-230 (2005).
US Pharmacopeia, (711) Dissolution/Physical Tests, pp. 2412-2414 (2005).
Guidance for Industry, Dissolution Test of Immediate Release Solid Oral Dosage Forms, U.S. Department of Health and Human Services, Food and Drug Administration, Center for Drug Evaluation and Research (CDER), Aug. 1997.
Tacha et al., "Casein Reduces Nonspecific Background Staining in Immunolabeling Techniques", The Journal of Histotechnology; vol. 15, No. 2; (1992).

* cited by examiner

*Primary Examiner* — Jacob Cheu
(74) *Attorney, Agent, or Firm* — Fish & Richardson P.C.

(57) ABSTRACT

The present invention relates to the field of dissolution measurement and, more particularly to methods for reproducible dissolution testing of pharmaceutical products such as allergen vaccines.

30 Claims, No Drawings

METHOD FOR DISSOLUTION TESTING OF PHARMACEUTICAL PRODUCTS

CROSS REFERENCE TO PRIOR APPLICATIONS

This application is the U.S. national phase of International Application No. PCT/DK2006/000739, filed Dec. 22, 2006, which claims priority from Danish Application No. PA 2005 01828, filed Dec. 23, 2005 and U.S. Provisional Application No. 60/753,714, filed Dec. 23, 2005. The disclosure of each application is incorporated herein by reference in its entirety. The International Application published in English on Jun. 28, 2007 as WO 2007/071257 under PCT Article 21(2).

TECHNICAL FIELD

The present invention relates to the field of dissolution measurement and, more particular to methods for reproducible dissolution testing of pharmaceutical products such as allergen vaccines.

BACKGROUND OF THE INVENTION

A solid pharmaceutical product, such as a tablet or capsule, is generally composed of a mixture of active ingredient(s) and excipient(s) (i.e., pharmacologically inactive ingredients). Predictable and reproducible drug absorption from a solid dosage form after oral administration depends on several factors such as the release of the drug substance from the drug product and the dissolution or solubilization of the drug under physiological conditions. In case of drugs such as orodispersible allergen vaccines, it is very important that the dosage form disperse instantaneously upon contact with the saliva of the oral cavity in order to ensure that as much as possible of the active ingredient is presented to the mucosa of the oral cavity.

Because of the critical nature of the release of the drug substance from the drug product and the dissolution or solubilization of the drug, dissolution testing is often relevant to the prediction of in-vivo performance of a drug. Since in-vivo bio-studies tend to be expensive and time consuming, and ethical concerns can limit the desirability of these studies in humans, in-vitro drug dissolution tests are desirable as a low-cost and low-risk alternative.

Drug approving authorities such as EMEA and the FDA often require pharmaceutical companies to determine the drug release characteristics of any new pharmaceutical product in order to obtain approval and such testing can also be required as an on-going quality parameter.

Various protocols have been developed for conducting such in-vitro dissolution tests, and are routinely used for both product development and quality assurance. Often, drug dissolution testing is conducted using recommended compendial methods and apparatus, such as the U.S. Pharmacopoeia and the European Pharmacopoeia e.g. USP 28 <711> and EP 5.0, 2.9.3. Dissolution profiles are often used by the approving authorities such as FDA and EMEA for accepting products, waive bioequivalence requirements and support requests for other bioequivalence requirements than the recommended. Dissolution media typically used in such tests are e.g. phosphate buffers, water and citrate buffers. Four different types of dissolution apparatus, based on different stirring methods are commonly available commercially and have compendial recognition. These apparatus are known as: paddle, basket, flow-through, and reciprocating cylinder. Of the four types of apparatus, the paddle apparatus is the most commonly used. Several standard paddle-type drug dissolution testing apparatus are known, such as those manufactured by Varian Inc., Distek Inc. and others. While exact protocols and apparatus vary, all drug dissolution test methods involve placing the pharmaceutical product into an aqueous dissolution medium (e.g. water and/or buffers), and applying some form of agitation to the dissolution medium in order to promote disintegration and dissolution of the product under test.

Blanco-Prieto et al., Int. J. Pharm. 184 (2), 1999, 243-250, disclose a test medium for studying the release kinetics of a somatostatin analogue from poly(D,L-lactide-co-glycolide) microspheres. The test media were phosphate buffer saline (PBS) in different pH and molarities, and with or without 1, 5 and 10% bovine serum albumin (BSA) or 1, 4 and 10% human serum albumin (HSA). The concentration of the somatostatin analogue was subsequently determined by HPLC.

The immune system is accessible through i.a. the oral cavity and oromucosal, e.g. sublingual administration of allergens is a known route of administration. It is as for most pharmaceuticals very important to administer a correct dosage of an allergen to a patient. The dissolution testing conditions should be based on the physicochemical characteristics of the drug substance and the environmental conditions the dosage form might be exposed to after oral administration. Many of the known dissolution media are developed for oral formulations intended to be swallowed and absorbed through the gastrointestinal tract and are not suitable for pharmaceutical products intended to be dispersed in the mouth such as under the tongue and act in the oral cavity.

Furthermore, proteins are often unstable in solution, especially when they are in low concentration and may denaturate with adsorption to surfaces such as glass surfaces as a result.

The active ingredient in an allergen tablet is a mixture of proteins some of which may have a low stability in solution, chemical as well as physical, and stability considerations are therefore of great importance for the proper choice of dissolution medium. Commonly used dissolution media are not suitable for dissolution of solid dosage forms containing proteins such as allergens in low concentration due to physical instability or denaturation in solution.

A dissolution medium which enables reproducible dissolution of protein containing products, which is pharmaceutically relevant and which overcomes the problems with adsorption to the surfaces remains therefore highly desirable.

SUMMARY OF THE INVENTION

The present invention provides a method for determining the amount of active ingredient released from a pharmaceutical solid dosage form wherein the active ingredient is one or more proteins, said method comprising the steps of:
(a) allowing said solid dosage form to release the active ingredient in a dissolution medium comprising from 0.05 to 2.0% casein and from 0.005 to 1.0 M phosphate buffered saline, and having a pH in the range of 6 to 8.5; and
(b) determining the amount of active ingredient in the solution.

DETAILED DESCRIPTION OF THE INVENTION

Dissolution Testing

It has been found that by using the method according to the invention for determining the amount of active ingredient released from a solid dosage form of a pharmaceutical protein containing product, especially solid dosage forms containing proteins in low doses such as allergens and highly potent proteins, it is possible to obtain a reproducible and physiologically relevant dissolution testing of a pharmaceutical product without the aforementioned problems with e.g. denaturation and adsorption.

According to the invention a method for determining the amount of active ingredient released from a pharmaceutical solid dosage form wherein the active ingredient is one or more proteins, said method comprising the steps of:
(a) allowing said solid dosage form to release the active ingredient in a dissolution medium comprising from 0.05 to 2.0% casein and from 0.005 to 1.0 M phosphate buffered saline, and having a pH in the range of 6 to 8.5; and
(b) determining the amount of active ingredient in the solution
is provided.

In one aspect of the invention, the dissolution medium has a pH in the range of 6 to 8.5. In another aspect of the invention, the dissolution medium has a pH in the range of 6 to 8. In another aspect of the invention, the dissolution medium has a pH in the range of 6.2 to 7.6. In another further aspect of the invention, the dissolution medium has a pH in the range of 6.4 to 7.4. In another aspect of the invention, the dissolution medium has a pH in the range of 6.6 to 7.3. In another aspect of the invention, the dissolution medium has a pH in the range of 6.7 to 7.2. In another aspect of the invention, the dissolution medium has a pH in the range of 6.7 to 6.9.

In one aspect of the invention, the dissolution medium comprises from 0.1 to 1.0% casein. In a further aspect of the invention, the dissolution medium comprises from 0.3 to 0.7% casein. In another aspect of the invention, the dissolution medium comprises about 0.5% casein.

Whenever the percentage of a substance (such as for example casein) in a liquid medium is provided herein, the percentage is provided as w/v %. The w/v % is calculated based on gram in 100 ml liquid.

Phosphate buffered saline (in the following also abbreviated PBS) is a phosphate buffered salt solution commonly used. The buffer helps to maintain a constant pH. In one aspect of the invention, the phosphate buffered saline has a molarity below 1.0M. In a further aspect of the invention, the phosphate buffered saline has a molarity below 0.5M. In yet a further aspect of the invention, the phosphate buffered saline has a molarity below 0.1M. In another aspect of the invention, the phosphate buffered saline has a molarity above 0.005M. In another aspect of the invention, the phosphate buffered saline is from 0.005 to 1.0 M phosphate buffered saline. In yet another aspect of the invention, the phosphate buffered saline is from 0.005 to 0.5 M phosphate buffered saline. In a further aspect of the invention, the phosphate buffered saline is from 0.005 to 0.1 M phosphate buffered saline. In another aspect of the invention, the phosphate buffered saline is 0.005-0.05M phosphate buffered saline. In another aspect of the invention, the phosphate buffered saline is about 0.01M phosphate buffered saline. In a further aspect of the invention, the PBS comprises sodium chloride, potassium chloride, monobasic potassium phosphate and dibasic sodium phosphate.

Whenever a molarity is provided for PBS herein, it is the molarity of phosphate ions in the PBS, which is referred to.

The dissolution medium optionally further comprises a non-ionic detergent such as a non-ionic detergent selected from the group consisting of Tween-20, Tween-80, Span 20 or Span 80.

In one aspect of the invention, the dissolution medium is a 0.01 M phosphate buffered saline comprising 0.08% (w/v) sodium chloride, 0.02% (w/v) potassium chloride, 0.02% (w/v) monobasic potassium phosphate and 0.144% (w/v) dibasic sodium phosphate, and casein sodium salt 0.5% (w/v) and deionized water.

The term "casein" refers as used herein to casein or a salt thereof, such as e.g. a casein sodium salt.

The dissolution medium can be prepared by mixing phosphate buffered saline (e.g. 10× the strength), casein sodium salt and deionized water and adjusting the pH with hydrogen chloride, such as 0.2 M hydrogen chloride.

In one aspect of the invention, the dissolution buffer comprises about 0.5% (w/v) casein, about 0.01 M PBS, and has a pH of about 6.8.

In-vitro dissolution testing of a solid dosage form such as a fast-dispersing solid dosage form, can be used for assessing batch-to-batch quality of a drug product, guide development of new formulations, ensure continuing product quality and performance after changes, such as changes in the formulation, the manufacturing process, the site of manufacture, and the scale-up of the manufacturing process, and testing of the shelf life of a product. In one aspect of the invention, the dissolution testing is used for assessing batch-to-batch quality of a solid dosage form. In another aspect of the invention, the dissolution testing is used for testing of the shelf life of a solid dosage form.

Duration of Dissolution

The solid dosage form is allowed to release the active ingredient in a period of time thereby forming at least a partial solution of the solid dosage form before withdrawing a sample. Depending on the particular solid dosage form and e.g. the apparatus and the agitation chosen, the time before withdrawing the sample for determination of active ingredient will depend on the particular product to be tested and can be determined by a skilled person within the field. In one aspect of the invention, the solid dosage form is allowed to release the active ingredient for a period of time at least long enough for obtaining a homogenous solution making it possible to obtain reproducible results of tested samples. After a certain time period at least some of the active ingredient has been released and the sample is can be filtered before determining the amount of active ingredient released at a given time period. In one aspect of the invention, the sampling is performed within 15 min. of placing the solid dosage form in the dissolution apparatus. In a further aspect of the invention, the sampling is performed within 10 min. of placing the solid dosage form in the dissolution apparatus. In yet a further aspect of the invention, the sampling is performed within 5 min. of placing the solid dosage form in the dissolution apparatus. In yet a further aspect of the invention, the sampling is performed within 3 min or within 1 min. of placing the solid dosage form in the dissolution apparatus.

Dissolution Specifications

Depending on the drug product to be tested, single point specifications, two point specifications or dissolution profiles can be used as described in e.g. *U.S. Pharmacopeia* (USP) 28 <711> and *European Pharmacopoeia* (EP) 5.0, 2.9.3. Typically single point specifications are used for routine quality testing for highly soluble and rapidly dissolving drug products. Two point specifications are typically used for characterizing the quality and as routine quality control testing of controlled release dosage forms.

Apparatus

Any apparatus suitable for dissolution of a drug product can be used. Currently, the most commonly employed dissolution test methods are (1) the basket method and (2) the paddle method. These two apparatus in-vitro dissolution methods are described in USP 28 <711> and EP 5.0, 2.9.3. Other dissolution procedures also described in the US and in the European Pharmacopoeia are the reciprocating cylinder method and the flow-through cell system method. In many cases it will be desirable to obtain a suitable in-vivo correlation with in-vitro release data and the final choice of any of these current methodologies or other alternatives/modifications will depend on the particular drug product to be tested. Above mentioned dissolution methodologies and apparatus can generally be used either with manual sampling or with automated procedures. In one aspect of the invention, the paddle apparatus method is used with either manual or automatic sampling.

Agitation

After having immersed the drug product in a suitable dissolution vessel, in general mild agitation conditions should be maintained during dissolution testing in order to avoid denaturation or foaming, and at the same time obtain a homogenously distribution in the vessel. Using the basket method, the agitation (or stirring speed) is generally 50-100 rpm and with the paddle method, it is generally 50-150 rpm. In one aspect of the invention, the dissolution apparatus is a paddle apparatus. The volume of the dissolution medium is generally 500, 900, or 1000 mL. However, any appropriate volume may be chosen.

Determining the Amount of Active Ingredient

Any appropriate method for determining the amount of active ingredient may be used which is suitable in relation to the active ingredient to be measured and the dissolution medium.

In one aspect of the invention, the allergen content of a solid dosage form can be determined by routine immune assays such as ELISA, FIA, LIA and RID against extract components such as major allergens using a standardised antibody mixture raised against the extract obtained using standard methods, e.g. antibodies raised in mouse or rabbit, or a pool of allergic patients sera.

In one aspect of the invention, the assay is an ELISA assay.

Solid Dosage Form

The term "solid dosage form" refers in the present context to a unit dosage form that is not a liquid, or a powder when it is administered in the oral cavity, thus "solid dosage forms" refers to e.g. tablets containing a unit dose of the active ingredient. The solid dosage form may be in the form of tablets, capsules, lozenges or caplets. In one aspect of the invention, the solid 0.5 dosage form is a tablet.

The term "fast dispersing dosage form" refers in the present context to dosage forms which disperse in less than about 90 seconds, preferably in less than about 60 seconds, preferably in less than about 30 seconds, more preferably in less than about 20, even more preferably in less than about 10 seconds in the oral cavity, even more preferred in less than about 5 seconds, and most preferably in less than about 2 seconds after being received in the oral cavity. In one aspect of the invention, the solid dosage form is a fast dispersing solid dosage form. In a further aspect of the invention, the solid dosage form is a fast dispersing solid dosage form for oromucosal administration.

The term "oromucosal administration" refers to a route of administration where the dosage form is placed anywhere in the oral cavity such as e.g. under the tongue to allow the active ingredient to come in contact with the mucosa of the oral cavity or the pharynx of the patient in order to obtain a local or systemic effect of the active ingredient. An example of an oromucosal administration route is sublingual administration.

The term "sublingual administration" refers to a route of administration, where a dosage form is placed underneath the tongue in order to obtain a local or systemic effect of the active ingredient.

The term "pharmaceutical solid dosage form" as used herein refers to a solid dosage form comprising an active ingredient in an effective amount to be able to cure, alleviate or partially arrest the clinical manifestations of a given condition or disease and its complications.

Effective amounts for each purpose will depend on the severity of the disease or condition as well as the weight and general state of the subject. It will be understood that determining an appropriate dosage may be achieved using routine experimentation, by constructing a matrix of values and testing different points in the matrix, which is all within the ordinary skills of a trained physician or veterinary.

Using the method according to the invention it is possible to determine the amount of active ingredient released from a pharmaceutical solid dosage form even when the active ingredient is present at very low concentrations such as in solid dosage forms comprising allergens. In one aspect of the invention, the amount of the active ingredient (e.g. major allergens) in the dissolution sample is 1-50 ng/ml.

The term "active ingredient" refers in the present context to one or more proteins.

The term "protein" refers in the present context to a protein having a sequence of amino acids including any naturally occurring protein, a modified protein, a recombinant protein, a recombinant mutant protein, or any protein fragment thereof or mixtures of proteins.

The following list of useful proteins is provided for illustrative purposes and is in no way meant to limit the scope of the medically useful proteins that may be determined using the method according to the invention: allergens; mammalian proteins, such as, e.g. growth hormone, including human growth hormone and bovine growth hormone; growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumor necrosis factor-α and -β; enkephalinase; RANTES (regulated on activation normally T-cell expressed and secreted); human macrophage inflammatory protein (MIP-1-α); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-2, IL-4, IL-5, IL-10, IL-13, IL-15; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; oxytocin, vasopressin, adrenocorticotropin hormone and analogs, epidermal growth factor, prolactin, somatostatin, GLP-1 related compounds, gastrin tetragastrin, pentagastrin, urogastrin, secretin, enkaphalins, endorphins, angiotensins, thyrotropin releasing hormone, granulocyte colony stimulating factor, granulocyte macrophage colony stimulating factor, macrophage colony stimulating factor, renin, bradykinin, bacitracins, polymixins, colistins, tyrocidin, or gramicidins.

In the present context the term "allergen" refers to any protein such as a naturally occurring protein, a modified protein, a recombinant protein, a recombinant mutant protein, or any protein fragment thereof or mixtures of proteins that have been reported to induce allergic, i.e. IgE mediated reactions upon their repeated exposure to an individual.

Examples of naturally occurring allergens include pollen allergens (tree, weed, herb and grass pollen allergens), mite allergens (from e.g. house dust mites and storage mites), insect allergens (inhalant, saliva- and venom origin allergens), animal allergens from e.g. saliva, hair and dander from e.g. dog, cat, horse, rat, mouse, etc., fungi allergens and food allergens.

Important pollen allergens from trees, grasses and weeds are such originating from the taxonomic orders of Fagales, Coniferales, Lamiales, Pinales and Platanaceae including i.a. birch (*Betula*), alder (*Alnus*), hazel (*Corylus*), hornbeam (*Carpinus*), olive (*Olea*), cedar (*Cryptomeria* and *Juniperus*), Plane tree (*Platanus*), the order of Poales including i.a. grasses of the genera *Festuca, Lolium, Phleum, Poa, Cynodon, Dactylis, Holcus, Phalaris, Secale,* and *Sorghum* and the orders of Asterales and Urticales including i.a. weeds of the genera *Ambrosia, Artemisia,* and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are i.a. such originating from the genera *Alternaria, Cladosporium, Aspergillus* and *Penicillium*.

Examples of food allergens are allergens from wheat (e.g. Tri a 18-19), crustacean food including shrimp (e.g. Met e 1, Pen a 1, Pen l 1, Pen m 1 and Pen m 2), prawn, crab and lobster, fish (e.g. Gad c 1 and Sal s 1), hen's eggs (e.g. Gal d 1, Gal d 2), peanut (e.g. Ara h 1-8), soy (Gly m 1-4), cows' milk (Bos d 4-8), nuts such as almond (Pru du 4), brazil nut (Ber e 1, Ber e 2), cashew nut (Ana o 1-3), hazelnut (e.g. Cor a 1.04, Cor a 2, Cor a 8) and walnut (e.g. Jug n 1-2, Jug r 1-3), celery (Api g 1, Api g 4, Api g 5), mustard (Sin a 1 and Bra j 1) and sesame seed (Ses i 1-6), such as allergens from wheat (e.g. Tri a 18-19), hen's eggs (e.g. Gal d 1, Gal d 2), peanut (e.g. Ara h 1-8), soy (Gly m 1-4), cows' milk (Bos d 4-8).

Examples of recombinant allergens include but are not limited to proteins/peptides from plant pollens, grass pollens, tree pollens, weed pollens, insect venom, dust and storage mite proteins, animal dander, saliva, fungal spores and food allergens (i.e., peanut, milk, gluten and egg) prepared using recombinant techniques. Recombinant allergens can be obtained e.g. on a large scale by using microbial expression systems that may be grown on fermenters, produced by recombinant DNA techniques, or chemical precursors or other chemicals when synthesized chemically. In one aspect of the invention, the allergen is rBet v 1, rAln g 1, rCor a 1, rCar b 1, rCry j 1, rCry j 2, rOle e 1, rAmb a 1, rArt v 1, rCyn d 1, rDac g 1, rDac g 5, rLol p 1, rLol p 5, rPhl p 1, rPhl p 5, rPoa p 1, rPoa p 5, rSor h 1, rDer f 1, rDer f 2, rDer p 1, rDer p 2, rEur m 1, rEur m 2, rGly d 2, rLep d 2, rTyr p 2, rBla g 1, rBla g 2, rFel d 1, rCan f 1, rCan f 2, rBos d 2, rEqu c 1, rEqu c 2, rMus m 1, rRat n 1, rApis m 1, rApi m 1, rApi m 2, rVes v 1, rVes v 2, rVes v 5, rDol a 5, rDol m 1, rDol m 2, rDol m 5, rPol a 1, rPol a 2, rPol a 5, rAlt a 1 or rCla h 1.

Examples of a modified allergen include allergens, which in naturally occurring form are associated with allergic disease conditions in sensitive subjects, wherein said modified recombinant allergen is altered compared to the naturally occurring allergen. Included are allergen variants containing a few amino acid exchanges, allergen mutants, oligomers, fragments, deletion variants, hybrid molecules, myristylated, glycosylated, palmitoylated and phosphorylated allergens and other variants. The modified allergen can be produced by any method suitable such as a site-directed mutagenesis method, a PCR method, chemical synthesis and a mixture of these methods.

A recombinant mutant allergen differs from the wild type in that the genes for the allergens have been modified by genetic manipulation methods such that the polypeptides which they encode exhibit substitutions, deletions and/or additions of individual or several amino acids as compared with the wild type. Examples of a recombinant mutant allergen include allergen substitution variants, addition variants, oligomers, fragments, deletion variants, hybrid molecules and other variants.

In one aspect of the invention, the method according to the invention is used for measuring dissolution of a solid dosage form which is an allergen composition. In a further aspect of the invention, the allergen solid dosage form is in form of a fast-dispersing dosage form for oral administration intended for dispersing instantaneously or quickly in the mouth upon contact with the saliva in order to ensure maximum exposure of allergen to immune competent tissue of the mucosa before swallowing.

In one aspect of the invention, the active ingredient in the solid dosage form is one or more allergen(s) selected from the group of Bet v 1, Aln g 1, Cor a 1 and Car b 1, Que a 1, Cry j 1, Cry j 2, Cup a 1, Cup s 1, Jun a 1, Jun a 2, Jun a 3, Ole e 1, Lig v 1, Syr v 1, Pla l 1, Pla a 1, Pla a 2, Amb a 1, Amb a 2, Amb t 5, Art v 1, Art v 2, Art v 3, Par j 1, Par j 2, Par j 3, Sal k 1, Ave e 1, Cyn d 1, Cyn d 7, Dac g 1, Fes p 1, Hol l 1, Lol p 1, Lol p 5, Pha a 1, Pas n 1, Phl p 1, Phl p 2, Phl p 3, Phl p 4, Phl p 5, Phl p 6, Poa p 1, Poa p 5, Sec c 1, Sec c 5, Sor h 1, Der f 1, Der f 2, Der f 3, Der f 7, Der p 1, Der p 2, Der p 3, Der p 7, Der m 1, Eur m 1, Eur m 2, Gly d 1, Gly d 2, Lep d 1, Lep d 2, Blo t 1, Tyr p 2, Bla g 1, Bla g 2, Per a 1, Per a 3, Per a 7, Fel d 1, Fel d 2, Fel d 3, Fel d 4, Can f 1, Can f 2, Bos d 2, Equ c 1, Equ c 2, Equ c 3, Mus m 1, Rat n 1, Apis m 1, Api m 1, Api m 2, Ves v 1, Ves v 2, Ves v 5, Ves f 5, Ves g 5, Ves m 1, Ves m 2, Ves m 5, Ves p 5, Ves s 5, Ves vi 5, Doi m 1, Dol m 2, Doi m 5, Doi a 5, Pol a 1, Pol a 2, Pol a 5, Sol i 1, Sol i 2, Sol i 3 and Sol i 4, Alt a 1, Alt a 3, Alt a 4, Alt a 5, Alt a 6, Cla h 1, Cla h 2, Cla h 6, Asp f 1, Bos d 4, Mal d 1, Mal d 3, Gly m 1, Gly m 2, Gly m 3, Ara h 1, Ara h 2, Ara h 3, Ara h 4, Ara h 5 or hybrids of any of these.

In the present context, Der p 2 and Der f 2 allergens is also referred to as "Der gr. 2" allergens. Quantification of Der gr. 2 allergens thus means quantification of the total amount of Der p 2 and Der f 2 allergens.

In one aspect of the invention, the active ingredient is one or more allergen extract(s).

In the present context, the expression "allergen extract" refers to any extract obtained by extraction of a biological allergen source material as generally described in "Allergenic extracts", H. Ipsen et al, chapter 20 in Allergy, principle and practise (Ed. S. Manning) 1993, Mosby-Year Book, St. Louis. Such extract may be obtained by aqueous extraction of water soluble material followed by purification steps like filtration to obtain the solution i.e. the extract. The extract may then be subjected to further purification and/or processing like freeze-drying removing substantially all the water. Generally, an allergen extract comprises a mixture of proteins and other molecules. Allergen proteins are often classified as a major allergen, an intermediate allergen, a minor allergen or no classification. An allergen extract generally comprises both major and minor allergens. Major allergens will generally constitute approximately 5-15% of an average allergen extract, more often about 10%. Classification of an allergen is based on an assessment of the clinical importance of the particular allergen and is given below. The extract may be i.e. in an aqueous form or in a lyophilized form.

Examples of important major allergens found in an extract include grass group 1 and 5 and 6 allergens (e.g. Phl p 1, 5, and 6), dust mite group 1 and 2 allergens (e.g. Der p 1, Der p 2), tree pollen allergens 1 and 2 (e.g. Bet v 1, Cry j 1, Cry j 2), ragweed pollen allergens 1 and 2 (Amb a 1, Amb a 2), cat allergen 1 (i.e. Fel d 1).

The expression "biological allergen source material" as used herein refers to any biological material comprising one or more allergens. Examples of such materials are acarids PMB (Pure Mite Body) or WMC (Whole Mite Culture), defatted or non-defatted pollens from e.g. grasses, herbs, weeds and trees, animal hair and dander, pelt, fungi mycelia and spores, insect bodies, venom or saliva and foods.

Biological allergen source materials may comprise contaminating materials, such as foreign pollen and plant and flower debris from an allergen pollen source material. The maximum level of accepted contamination with pollen from other species is 1%. It should also be devoid of flower and plant debris, with a limit of 5% by weight.

In one aspect of the invention the active ingredient in the solid dosage form is one or more allergen extract(s) of a biological allergen source material selected from the group of *Phleum pratense, Dermatophagoides farinae, Dermatophagoides pteronyssinus, Betula verrucosa, Corylus avellana, Alnus glutinosa, Cryptomeria japonica, Ambrosia artemisiifolia, Ambrosia trifida, Artemisia vulgaris* and *Felis domesticus*.

In a further aspect of the invention, the active ingredient is an extract from pollen of the Timothy grass—*Phleum pratense*—comprising a mixture of proteins including but not limited to one or more of the allergens Phl p 1, Phl p 2, Phl p 3, Phl p 4, Phl p 5, Phl p 6, Phl p 7, Phl p 11, Phl p 12, Phl p 13. In a further aspect of the invention, the active ingredient is a mix of *Dermatophagoides pteronyssinus* extract and *Dermatophagoides farinae* extract, comprising a mixture of proteins including but not limited to one or more of the allergens Der p 2, Der f 2, Der p 1 and Der f 1.

In another aspect of the invention, the active ingredient is an extract from pollen of the Birch tree—*Betula verrucosa*—comprising a mixture of proteins including but not limited to one or more of the allergens Bet v 1, Bet v 2, Bet v 3, Bet v 4, Bet v 6, Bet v 7.

In another aspect of the invention, the active ingredient is an extract from pollen of short ragweed—*Ambrosia artemisiifolia*—and/or giant ragweed—*Ambrosia trifida*—comprising a mixture of proteins including but not limited to one or more of the allergens Amb a 1, Amb a 2, Amb a 3, Amb a 5, Amb a 6, Amb a 7 and Amb t 5.

The term "allergen vaccine" as used in the present context comprises at least one allergen either originating from the same allergenic source or originating from different allergenic sources e.g. grass group 1 and grass group 5 allergens or mite group 1 and group 2 allergens from different mite and grass species respectively, weed antigens like short and giant ragweed allergens, different fungi allergens like alternaria and cladosporium, tree allergens like birch, hazel, hornbeam, oak, Japanese cedar and alder allergens, food allergens like peanut, soybean and milk allergens.

In a further aspect of the invention, the dosage forms to be measured are allergen tablets in form of solid dosage forms as described in e.g. WO2004047794 (ALK-Abelló), WO2004075875 (ALK-Abelló), EP 278 877 (Medibrevex), WO 200061117 (Scherer), or WO2000057856 (Pierre Fabre Medicament).

In a further aspect of the invention, the solid dosage form to be used in the method according to the invention is a fast dispersing solid dosage form. Especially suitable solid dosage forms for dissolution by the method according to the invention are e.g. as described in WO2004047794 comprising a solid network of the allergen and any water-soluble or water-dispersible matrix. The network is obtained by subliming solvent from a composition in the solid state, the composition comprising a solution of the allergen and the matrix such as obtained by lyophilization. Pharmaceutically acceptable excipients forming part of the matrix in the fast-dispersing solid dosage form are matrix forming agents and additionally other suitable excipients such as antacids, diluents, enhancers, mucoadhesive agents, flavouring agents, taste masking agents, preservatives, antioxidants, surfactants, viscosity enhancers, colouring agents, pH modifiers, sweeteners, adjuvants, disintegrants, lubricants etc. These excipients are all selected in accordance with conventional pharmaceutical practice in a manner understood by persons skilled in the art of formulating allergen therapeutics. Examples of matrix forming agents include excipients derived from animal or vegetable proteins such as gelatines, dextrins and soy, wheat and psyllium seed proteins; gums such as acacia, guar, agar and xanthan; polysaccharides; starch and modified starch, alignates; carboxymethylcellulose; carrageenans; dextrans; pectins; synthetic polymers such as polyvinylpyrrolidone; and polypeptide/protein or polysaccharide complexes such as gelatine-acacia complexes. Gelatines are a heterogeneous mixture of water soluble colloid macromolecules. Such heterogeneous mixtures of average molecular weights distribution may be obtained from hydrolytic action on collagen rich material of animal origin such as bone, skin, tendons, ligaments etc. Gelatines may be derived from mammal e.g. cattle, pig or non-mammals e.g. warm or cold water fish. Gelatines can be hydrolysed or non-hydrolysed, cross-linked or non-cross-linked. They can further be of a gelling or non-gelling type, the non-gelling type typically being derived from cold water fish. In another particular aspect of the invention, starch is used. Starches are complex mixtures of carbohydrate polymers. As examples of other suitable matrix forming agents mention can be made of sugars such as mannitol, dextrose, lactose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

In one aspect of the invention, the solid dosage form comprises one or more ingredients selected from the group consisting of mannitol, cellulose, croscarmellose sodium, silica and/or magnesium stearate.

In a further aspect of the invention, the solid dosage form comprises one or more ingredients selected from the group consisting of mannitol and fish gelatine.

In one aspect of the invention, the solid dosage form is as described in WO2004047794 example 1 wherein the active ingredient is an extract of *Phleum pratense*.

In another aspect of the invention, the solid dosage form is as described in WO2004047794 wherein the active ingredient is a mix *Dermatophagoides pteronyssinus* extract and *Dermatophagoides farinae* extract.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value.

EXAMPLES

Materials and Methods

Solid Dosage Forms
Dosage Forms Containing *Phleum pratense* Extract.

Dosage form 1 and 2 containing Phleum pratense as the allergen extract were prepared as described in example 1 in WO2004047794 with the ingredients as described in below Table 1.

TABLE 1

Different dosage forms containing *Phleum pratense*

| Ingredients | Dosage form 1 % w/w | Dosage form 2 % w/w | Dosage form 3 % w/w |
| --- | --- | --- | --- |
| Gelatine Fish | 4.0% | 6.5% | 6.0% |
| Mannitol | 3.0% | 5.5% | 5.08% |
| Grass Pollen Extract (*Phleum pratense*) SQ-T | 125000 or 25000 or 2500 | 75000 or 25000 or 2500 | 75000 or 25000 |
| NaOH | qs to pH 7.5 | qs to pH 7.5 | qs to pH 7.5 |
| Purified water | qs to 250 mg | qs to 250 mg | qs to 250 mg |
| Total %/Wet fill weight | 100% | 100% | 100% |
| Dried unit weight (Theoretical value) | 17.5 mg (excluding NaOH) | 30.0 mg (excluding NaOH) | 27.7 mg (excluding NaOH) |

SQ-T: The SQ-T unit is determined in accordance with ALK-Abelló A/S's "SQ biopotency"-standardisation method (http://www.alk-abello.com) and is assigned to tablets. The standardization procedure comprises an evaluation of the quality of the allergen extract relative to an internal standard, quantification of the most important major allergens and comparison to the internal standard, adjustments of the content of major allergen(s) relative to the internal reference, yielding constant level(s) of major allergen(s) relative to the SQ-T unit and measurement of the total allergenic activity, i.e. potency, of the allergen extract in terms of IgE binding relative to the internal standard.

Dosage forms with different amounts of Phleum pratense may be prepared using the same ingredients and method as described above.

Dosage Forms Containing *Dermatophagoides pteronyssinus* and *Dermatophagoides farinae* Extract.

Dosage form 4 containing Der gr. 2, Der p 1 and Der f 1 as the major allergens were prepared analogously to the methods described in WO2004047794.

Dissolution Method

In the following examples the dissolution method described in EP 5.0, 2.9.3 is used. The solid dosage form is immersed into a paddle apparatus containing 500 ml 37° C. dissolution medium. The rotation speed and the time for when samples are withdrawn are given in each example. Samples are filtered through a 0.22 μm membrane filter prior to analysis by an ELISA method. In the examples 1-4 the experiments were performed in three or six replicates (n=3 or n=6), the results are given as a mean of three or six values and for each example the number of replicates (n) is stated. The dissolution method described is validated. For the dosage form 3, 75000 SQ-T, and n=6, the intermediate precision (coefficient of variation) CVip is ≦15.5% and the repeatability (coefficient of variation) CVrep is ≦3.7%.

Preparation of Dissolution Medium 0.5% (w/v) Casein, 0.01 M PBS, pH 6.8.

The dissolution medium consists of 0.01 M phosphate buffered saline (concentrations in the final buffer are: 0.08% (w/v) sodium chloride, 0.02% (w/v) potassium chloride, 0.02% (w/v) monobasic potassium phosphate and 0.144% (w/v) dibasic sodium phosphate), casein sodium salt 0.5% (w/v) and deionized water. The dissolution medium is prepared by mixing phosphate buffered saline (10× the strength, Bie & Berntsen), casein sodium salt (ICN Biomedicals) and deionized water and adjusting the pH to 6.8 with 0.2 M hydrogen chloride.

The Enzyme-Linked Immunosorbent Assay (ELISA) for *Phleum pratense* Major Allergen 5 (Phl p 5)

The test was performed using ELISA technique based on Obispo et al, Allergy, 1997, 52, pg. 806-813.

The ELISA method measures the activity of *Phleum pratense* major allergen 5 (Phl p 5). Two monoclonal antibodies (ALK-Abello A/S, DK) reacting with different epitopes on the Phl p 5 molecule were coated on the microtiterplate the night over at 4° C. After washing (4 times with washing buffer, 0.01 M PBS, 0.050% Tween-20) and blocking the plate with blocking buffer (20% Caseinbuffer), samples/references, which then binds to the antibodies, were applied. After washing again (4 times with washing buffer) biotinylated rabbit polyclonal antibodies (ALK-Abello A/S, DK) against *Phleum pratense* antigens were applied to the wells and allowed to react.

After 4 times washing with wash buffer, streptavidin coupled to HRP (horse radish peroxidase) (DAKO, Denmark) was applied to the wells and allowed to react for 1 hour at room temperature (shaking). After washing 4 times with washing buffer, substrate (TMB, KEM EN TEC) for the HRP enzyme was applied and allowed to react for 20 min., where after the reaction was stopped with 0.5 N sulphuric acid. The colour developed was measured at 450 nm in a spectrophotometer e.g. Multilabel counter Victor 2.

Samples from dissolution experiments were diluted in ELISA dilution buffer (0.5% Casein, 0.01M PBS, 0.05%

Tween-20, pH 7.2) prior to ELISA analysis. Samples in the range 2.4-40 SQ-T/ml can be analysed with the Phl p 5 ELISA.

The Enzyme-Linked Immunosorbent Assay (ELISA) for Der qr. 2, Der p 1 and Der f 1

Quantification of the major allergens (Der gr. 2, Der p 1 and Der f 1) in the dissolution samples were done by ELISA for Der gr. 2, Der p 1 and Der f 1 as described above for Phl p 5 except that the rabbit polyclonal antibody was not biotinylated, and the streptavidin coupled to HRP was replaced by a goat anti-rabbit HRP coupled polyclonal antibody. The measured values were compared to a reference value. For each ELISA setup the major allergen of a tablet of the relevant dose strength was determined as reference for 100% dissolution. Comparison to labeled amount was also done when suitable. All ELISA analyses were performed immediately after the dissolution test was done.

Example 1

Testing of various dissolution media were performed using the dissolution method as described above using 50 rpm. Each sample taken from the dissolution vessel was diluted in an ELISA dilution buffer containing 0.5% casein, 0.01M PBS, 0.05% Tween-20, and with a pH of 7.2 to a concentration of major allergen within range of the ELISA standard curve. The dissolution was measured by above described ELISA assay for Phleum pratense.

The following dissolution media were tested: 0.01 M PBS, pH 6.8 (H), 0.3 M acetate buffer, 0.9% NaCl, pH 4.0 (I), 0.063 M HCl, pH 1.2 (J), and 0.5% casein, 0.01 M PBS, pH 6.8 (K). Samples were withdrawn at 5, 15, 60, 120 min. in experiment H), I), J) and K). The casein immediately precipitated in experiment A) through C). For the media in experiment D) through G) an ELISA standard curve for Phleum pratense was made.

The solid dosage forms tested were above described "Dosage form 1 or 2" containing Phleum pratense as the allergen extract at a dose of 75000 SQ-T in all experiments.

TABLE 2

Testing of various dissolution media.

| Experiment | Medium | Result |
|---|---|---|
| A | 0.1 M acetate buffer, 0.5% casein, 0.05% Tween, pH 4.0 | Precipitation of casein/not further used |
| B | 0.3 M acetate buffer, 0.9% NaCl, 0.5% casein, 0.05% Tween, pH 4.0 | Precipitation of casein/not further used |
| C | Citrate buffer 0.3 M, 0.9% NaCl, 0.5% casein, 0.05% Tween, pH 4.0 | Precipitation of casein/not further used |
| D | 0.5% casein, 0.01 M PBS, 0.05% Tween, pH 7.2 | Tested as standard ELISA diluent buffer. It was possible to obtain an ELISA standard curve. |
| E | 0.5% casein, 0.01 M PBS, 0.05% Tween, pH 6.8 | Tested as standard ELISA diluent buffer. It was possible to obtain an ELISA standard curve. |
| F | 0.5% casein, 0.01 M PBS, pH 6.8 | Tested as standard ELISA diluent buffer. It was possible to obtain an ELISA standard curve. |
| G | 0.01 M PBS, pH 6.8 | Tested as ELISA diluent buffer. Absorbance values were very low, no standard curve was obtained. |
| H | 0.01 M PBS, pH 6.8 | Tested as dissolution buffer. 50-60% release throughout the dissolution period |
| I | 0.3 M acetate buffer, 0.9% NaCl, pH 4.0 | Tested as dissolution buffer. All samples precipitated when diluted in standard ELISA diluent buffer due to precipitation of casein. |
| J | 0.063 M HCl, pH 1.2 | Tested as dissolution buffer. All samples precipitated when diluted in standard ELISA diluent buffer due to precipitation of casein. |
| K | 0.5% casein, 0.01 M PBS, pH 6.8 | Tested as dissolution buffer. Complete release in 5 min |

As it appears from above table 2 the medium with 0.5% casein, 0.01 M PBS, at a pH of 6.8 gave complete release within 5 min. and was suitable as ELISA diluent buffer. Also the medium D and E were suitable both as dissolution medium and ELISA diluent buffer.

Example 2

Above described dissolution method was performed using 50 rpm and samples withdrawn at 5, 10 and 15 min. The dissolution medium used was dissolution medium with 0.5% casein, 0.01 M PBS, pH 6.8. Each sample taken from the dissolution vessel was diluted in an ELISA dilution buffer containing 0.5% casein, 0.01M PBS, 0.05% Tween-20, and with a pH of 7.2, to a concentration of major allergen within range of the ELISA standard curve for Phleum pratense. The dissolution was measured by above described ELISA assay for Phleum pratense.

Dosage form 1, 2 and 3 all containing Phleum pratense as the allergen extract, prepared as described above, was used with different amounts of active ingredient.

TABLE 3

Dissolution of dosage form 1, 2 and 3 containing *Phleum pratense*.

| Dose | Dosage form | % released of labelled amount Mean, n = 6 | | |
|---|---|---|---|---|
| | | 5 min. | 10 min. | 15 min. |
| 125000 SQ-T | 1 | 95 | 99 | 101 |
| 75000 SQ-T | 2 | 90 | 93 | 95 |
| 75000 SQ-T | 2 | 89 | 91 | 93 |
| 75000 SQ-T | 2 | 90 | 91 | 92 |
| 75000 SQ-T | 3 | 83 | 84 | 84 |
| 75000 SQ-T | 3 | 86 | 89 | 89 |
| 75000 SQ-T | 3 | 88 | 92 | 92 |

Full release is seen at 5 minutes from all three dosage forms. The variation in the percentage released of labelled amount can be explained by the variation of the immunochemical analytical method used and the content of active ingredient in the dosage form not being exactly 100%.

Example 3

Above described dissolution method was performed using 50 rpm and samples were withdrawn at different time points (from 5 to 60 minutes). The dissolution medium used was dissolution medium with 0.5% casein, 0.01 M PBS, pH 6.8. Each sample taken from the dissolution vessel was diluted in an ELISA dilution buffer containing 0.5% casein, 0.01M PBS, 0.05% Tween-20, and with a pH of 7.2, to an activity of major allergen within range of the ELISA standard curve for *Phleum pratense*. The dissolution was measured by above described ELISA assay for *Phleum pratense*.

Results from dissolution of dosage form 1 containing Phleum pratense as the allergen extract, prepared as described above, are shown in table 4.

TABLE 4

Dissolution of dosage forms containing different strengths of *Phleum pratense*.

| Dose | Dosage form | % released of labelled amount Mean, n = 3 | | |
|---|---|---|---|---|
| | | 5 min. | 15 min. | 60 min. |
| 2500 SQ-T | 1 | 122 | 126 | 138 |
| 25000 SQ-T | 1 | 103 | 107 | 109 |
| 75000 SQ-T | 1 | 90 | 94 | 94 |

Full release is seen at 5 minutes for all three strengths. The variation in the percentage released of labelled amount can be explained by the variation of the immunochemical analytical method used and the content of active substance in the dosage form not being exactly 100%.

Example 4

Above described dissolution method was performed using 150 rpm and samples were withdrawn at different time points (from 30 sec. to 5 minutes). The dissolution medium used was dissolution medium with 0.5% casein, 0.01 M PBS, pH 6.8. Each sample taken from the dissolution vessel was diluted in an ELISA dilution buffer containing 0.5% casein, 0.01M PBS, 0.05% Tween-20, and with a pH of 7.2, to an expected concentration of major allergen within range of the ELISA standard curve for *Phleum pratense*. The dissolution was measured by above described ELISA assay for *Phleum pratense*.

Dosage form 3 containing *Phleum pratense* as the allergen extract, prepared as described above, was used.

TABLE 5

Dissolution of dosage forms containing *Phleum pratense* at 150 rpm.

| Dose | Dosage form | Dissolution % released of labelled amount Mean, n = 6 | | | |
|---|---|---|---|---|---|
| | | 30 sec. | 1 min. | 3 min. | 5 min. |
| 75000 SQ-T | 3 | 90 | 93 | 94 | |
| 75000 SQ-T | 3 | 99 | 100 | 101 | |
| 75000 SQ-T | 3 | 96 | 97 | 99 | |
| 75000 SQ-T | 3 | 95 | | 95 | 95 |

The results show that the drug substance is fully released within the first minute, implying that the drug substance is expected to be fully available for interaction with the oral mucosa within the first minute.

Example 5

Dissolution of dosage form 2 containing *Phleum pratense* as the allergen extract, 75000 SQ-T, was performed in one vessel on different days in order to analyse all the samples in the same ELISA assay as described above for *Phleum pratense*. The samples were stored at 2-8° C. for 0, 1, 2, 3, 4 and 7 days. Each sample taken from the dissolution vessel was diluted in an ELISA dilution buffer containing 0.5% casein, 0.01M PBS, 0.05% Tween-20, and with a pH of 7.2, to a concentration of major allergen within range of the ELISA standard curve for *Phleum pratense*. The dissolution was measured by above described ELISA assay for Phleum pratense at day 0.

TABLE 6

Stability of dissolution samples.

| Day | Mean release of labelled amount after 15 min (%), n = 1 |
|---|---|
| Day −7 | 101 |
| Day −4 | 98 |
| Day −3 | 93 |
| Day −2 | 99 |
| Day −1 | 101 |
| Day 0 | 99 |

No degradation of the dissolution samples was found. This shows that the dissolution medium is very stable and that samples can be stored at 2-8° C. for at least 7 days before analysis.

Example 6

Above described dissolution method was performed using 150 rpm and samples were withdrawn between 1 and 15 minutes. Each sample was tested in 3 or 6 replica (n=3 or n=6). The dissolution medium used was dissolution medium with 0.5% casein, 0.01 M PBS, pH 6.8. Each sample taken from the dissolution vessel was diluted in an ELISA dilution buffer containing 0.5% casein, 0.01M PBS, 0.05% Tween-20, and with a pH of 7.2, to a concentration of major allergen within range of the ELISA (Der gr. 2, Der p 1 and Der f 1) standard curve (0.39-50.0 ng/ml).

Dosage form 4 containing Der gr. 2, Der p 1 and Der f 1 as the major allergens, prepared as described above, was used with different amounts of active substance.

Quantification of the major allergens (Der gr. 2, Der p 1 and Der f 1) in the dissolution samples were done by ELISA for Der gr. 2, Der p 1 and Der f 1 as described above. The measured values were compared to a reference value. For each ELISA setup the major allergen of a tablet of the relevant dose strength was determined as reference for 100% dissolution. Comparison to labeled amount was also done when suitable. All ELISA analyses were performed immediately after the dissolution test was done.

TABLE 7

Dissolution of dosage forms containing different concentrations of Der gr. 2, Der p 1 and Der f 1 at 150 rpm.

| Dose | | 0.5 min. | 1 min. | 3 min. | 5 min. | 10 min. | 15. min. |
|---|---|---|---|---|---|---|---|
| Results as % Der gr. 2 major allergens content compared to a reference value corresponding to 100% released | | | | | | | |
| Low | n = 3 | 95 | 87 | 84 | 84 | 87 | 83 |
| Medium | n = 6 | | 76 | 77 | 74 | | |
| High | n = 3 | 114 | 110 | 104 | 104 | 104 | 106 |
| Results as % Der f 1 major allergen content compared to a reference value corresponding to 100% released | | | | | | | |
| Medium | n = 3 | | 89 | 89 | 88 | | |
| High | n = 3 | | 94 | | 93 | | 89 |
| Results as % Der p 1 major allergen content compared to a reference value corresponding to 100% released | | | | | | | |
| Medium | n = 3 | | 98 | 100 | 99 | | |
| High | n = 3 | | 112 | | 110 | | 108 |

The invention claimed is:

1. A method for determining the amount of active ingredient released from a pharmaceutical solid dosage form wherein the active ingredient is one or more proteins, said method comprising the steps of:
   (a) allowing said solid dosage form to release the active ingredient in a dissolution medium comprising from 0.05 to 2.0% (w/v) casein and from 0.005 to 1.0 M phosphate buffered saline, and having a pH in the range of 6 to 8.5; and
   (b) determining the amount of active ingredient in the solution.

2. The method according to claim 1, wherein the dissolution medium has a pH in the range of 6.2 to 7.6.

3. The method according to claim 2, wherein the dissolution medium has a pH in the range of 6.6 to 7.3.

4. The method according to claim 3, wherein the dissolution medium has a pH in the range of 6.7 to 6.9.

5. The method according to claim 1, wherein the dissolution medium comprises from 0.1 to 1.0% (w/v) casein.

6. The method according to claim 5, wherein the dissolution medium comprises from 0.3 to 0.7% (w/v) casein.

7. The method according to claim 6, wherein the dissolution medium comprises about 0.5% (w/v) casein.

8. The method according to claim 1, wherein the phosphate buffered saline is from 0.005 to 0.5 M phosphate buffered saline.

9. The method according to claim 8, wherein the phosphate buffered saline is from 0.005 to 0.1 M phosphate buffered saline.

10. The method according to claim 9, wherein the phosphate buffered saline is about 0.01M phosphate buffered saline.

11. The method according to claim 1, wherein the dissolution medium further comprises a non-ionic detergent such as a non-ionic detergent selected from the group consisting of Tween-20, Tween-80, Span 20 or Span 80.

12. The method according to claim 11, wherein the solid dosage form is a fast dispersing solid dosage form.

13. The method according to claim 12, wherein the solid dosage form is a fast dispersing solid dosage form for oromucosal administration.

14. The method according to claim 11, wherein the solid dosage form disperses in less than about 90 seconds, after being received in the oral cavity.

15. The method according to claim 1, wherein the active ingredient is one or more allergen extract(s).

16. The method according to claim 15, wherein the allergen extract comprise one or more allergens from the group consisting of grass group 1 and 5 and 6 allergens, dust mite group 1 and 2 allergens, tree pollen allergens 1 and 2, ragweed pollen allergens 1 and 2, and cat allergen 1.

17. The method according to claim 1, wherein the active ingredient is an extract of *Phleum pratense*.

18. The method according to claim 1, wherein the active ingredient is an extract of *Dermatophagoides pteronyssinus* and *Dermatophagoides farinae*.

19. The method according to claim 1, wherein the method for determining the amount of active ingredient is an ELISA method.

20. The method according to claim 1, wherein the release of active ingredient is carried out in a dissolution apparatus.

21. The method according to claim 20, wherein the rpm in the dissolution apparatus is 50-150 rpm.

22. The method according to claim 1, wherein the solid dosage form comprises one or more ingredients selected from the group consisting of mannitol, cellulose, croscarmellose sodium, silica and/or magnesium stearate.

23. The method according to claim 1, wherein the solid dosage form comprises one or more ingredients selected from the group consisting of mannitol and fish gelatine.

24. The method according to claim 1, wherein the dissolution testing is used for assessing batch-to-batch quality of a solid dosage form.

25. The method according to claim 1, wherein the dissolution testing is used for testing of the shelf life of a solid dosage form.

26. The method according to claim 1, wherein the amount of active ingredient in the solution is determined within 15 min of placing the solid dosage form in the dissolution medium.

27. The method according to claim 1, wherein the amount of active ingredient in the solution is determined within 10 min of placing the solid dosage form in the dissolution medium.

28. The method according to claim 1, wherein the amount of active ingredient in the solution is determined within 5 min of placing the solid dosage form in the dissolution medium.

29. The method according to claim 1, wherein the amount of active ingredient in the solution is determined within 3 min of placing the solid dosage form in the dissolution medium.

30. The method according to claim 1, wherein the amount of active ingredient in the solution is determined within 1 min of placing the solid dosage form in the dissolution medium.

* * * * *